United States Patent [19]

Miles et al.

[11] Patent Number: 4,500,402

[45] Date of Patent: * Feb. 19, 1985

[54] REFERENCE ELECTRODE

[75] Inventors: Ronald C. Miles, Cleveland; George W. Geren, Georgetown; R. W. Peel, Tellico Plains, all of Tenn.

[73] Assignee: Olin Corporation, Cheshire, Conn.

[*] Notice: The portion of the term of this patent subsequent to Mar. 5, 2002 has been disclaimed.

[21] Appl. No.: 373,204

[22] Filed: Apr. 29, 1982

[51] Int. Cl.³ .............................................. G01N 27/30
[52] U.S. Cl. ........................................ 204/242; 29/859;
156/86; 174/DIG. 8; 174/77 R; 204/252;
204/258; 204/290 F; 204/435; 427/126.5
[58] Field of Search ............... 204/435, 433, 420, 242,
204/252, 258, 290 F; 174/DIG. 8, 77 R;
29/859; 156/85, 86, 48, 49, 158, 304.2

[56] References Cited

U.S. PATENT DOCUMENTS

| Re. 30,447 | 12/1980 | Loyd et al. | 174/DIG. 8 |
|---|---|---|---|
| 3,291,714 | 12/1966 | Hall et al. | 204/256 |
| 3,382,121 | 5/1968 | Sherlock | 174/DIG. 8 |
| 3,451,609 | 6/1969 | Gillett | 174/DIG. 8 |
| 3,525,799 | 8/1970 | Ellis | 174/DIG. 8 |
| 3,582,457 | 6/1971 | Barthell | 174/DIG. 8 |
| 3,843,506 | 10/1974 | Jerrold-Jones | 174/DIG. 8 |
| 3,853,732 | 12/1974 | Brand et al. | 204/195 |
| 3,959,107 | 5/1976 | Horner et al. | 204/420 |
| 4,105,509 | 8/1978 | Jungck | 204/1 T |
| 4,163,698 | 8/1979 | Kuo et al. | 204/1 T |
| 4,206,786 | 6/1980 | Wetmore | 174/DIG. 8 |
| 4,240,879 | 12/1980 | Dobson | 204/433 |

FOREIGN PATENT DOCUMENTS 1304849 1/1973 United Kingdom .

OTHER PUBLICATIONS

"J. V. Dobson, Potentials of the Palladium Hydride Reference Electrode between 25° and 195° C.", 35 Journal of Electroanalytical Chemistry pp. 129–135, (1972).

Primary Examiner—T. Tung
Attorney, Agent, or Firm—Ralph D'Alessandro; Donald F. Clements; Thomas P. O'Day

[57] ABSTRACT

A wire reference electrode and a method of employing the wire reference in an electrolytic cell is provided wherein the wire reference electrode comprises a lead-in wire portion, a reference wire portion, a sealing material to seal the junction of the lead-in and wire reference portions, and a heat shrinkable insulating material.

44 Claims, 4 Drawing Figures

REFERENCE ELECTRODE

BACKGROUND OF THE INVENTION

This invention relates generally to electrolytic cells and more particularly to wire reference electrodes and the method of utilizing wire reference electrodes to monitor voltage levels within the cell.

Typically the voltages of electrodes in either diaphragm type of chloralkali electrolytic cells or the more recently developed filter press membrane type of chloralkali electrolytic cells have been measured by use of a Luggin capillary tube that is positioned adjacent the electrode and which passes through the cell housing or electrode frame to a reference electrode placed outside of the cell. Such a Luggin capillary tube is inserted through the cell wall on top of the electrolytic cell by being passed through a polyethylene grommet or other appropriate seal and extended downwardly to a position adjacent the center of the electrode, for example, a cathode. The Luggin capillary tube is then connected by a salt bridge or liquid junction to a separate calomel reference electrode situated externally of the cell. This system of measuring electrode voltages does not permit the positioning of the reference electrode physically in the environment and at the exact location where the electrode potential to be measured exists. This method of measuring electric potential for electrodes is better suited for laboratory testing where electrode potentials must be measured.

The use of Luggin capillaries in electrolytic cells that generate gases creates further problems which are well known in the art. The Luggin capillary tube must have a continuous or unbroken stream of electrolyte in the tube throughout its length. One proven method of initially achieving this is by drawing the electrolyte through the tube by a syringe or other type of suction device in order to have sufficient electrolyte flow to obtain readings. However, gas generation creates bubbles that can block the relatively small capillary tube opening after the suctioning of electrolyte through the tube. This blockage, caused by the nucleation and growth of bubbles around the mouth of the tube, blocks the flow of electrolyte and causes a break to occur in the continuous stream of electrolyte along the tube's entire length. A similar obstruction can be created merely by the transfer or deposition of bubbles from the solution which were caused by a high level of agitation or rapid flow rate of the electrolyte fluid in the cell adjacent the electrode surfaces. Additionally, concentrated electrolyte solutions can salt out or freeze in the tube, thereby blocking liquid flow through the tube. To avoid this, once the salt bridge is established additional dilute electrolyte is normally fed into the tube.

It is also possible that the continuous stream of electrolyte which must be maintained through the Luggin capillary tube to the saturated calomel reference electrode is not identical to the electrolyte to which the electrode for which the potential is being recorded is exposed. This occurs when the dilute electrolyte solution flow is maintained downwardly through the capillary tube from an external reservoir into the cell electrolyte to avoid the gas bubble blockage at the tube's mouth or blockage within the tube from the aforementioned salting out of electrolyte. This flood of dilute solution does not permit an exact initial voltage reading to be obtained since the dilution of the electrolyte changes the measured voltage. In fact, this situation severely limits the utility of Luggin capillaries in conjunction with a saturated calomel reference electrode since they typically provide a potential recording only for that short window of time when solution is flowing through the tube and are not suitable for continuous or extended potential measurements.

Any of these conditions affect the accuracy of the reading obtained from the reference electrode using a Luggin capillary and, in fact, may obstruct the entire operation of the Luggin capillary.

Attempts to use Luggin capillaries in commercial electrolytic cells have proven them not to be suitable for commercial operations because of the practical problems encountered and their inherent limitations beyond those already enumerated. For example, the occurrence of an alternating current (AC) signal or ripple in the plant power supply will create rapid voltage changes which cannot be sensed by Luggin capillaries. Although these rapid voltage changes are not necessarily detrimental to the electrolysis, the potential in the Luggin capillaries cannot change rapidly enough and will, therefore, affect the reference electrode and its readings. Additionally, the length of the capillary tubes required for commercial sized cells could extend to twenty feet in length in order to connect to the external reference electrode. This length of tubing demands a very high internal pressure in order to keep the solution flowing and sweep any gas bubbles out of the tubing. If the necessary pressure to accomplish this is approached, the capillary tubes tend to leak from cracks or other failures or they pop off of their fittings. The latter event results in the spraying of hazardous caustic or other electrolyte about the cell plant building.

An obstruction problem can also result where salt bridges or liquid junctions are used with reference electrodes. These can become clogged, providing the same type of a problem encountered with gas bubble in the measurement of the potential and operation of the electrodes.

The desire to obtain electrical potential readings in the exact location where the potential to be measured exists by the insertion of reference electrodes into the cell has created additional problems. The harsh effect on the reference electrodes of the electrolytes encountered when the reference electrodes are inserted within the cell has been a persistent problem affecting the durability of the materials used to construct these electrodes. The corrosiveness of the anolyte and catholyte fluids tends to destroy the materials used. Reference electrodes with large diffuse Luggin openings also have been employed in attempts to avoid blockage problems. However, these electrodes have an electrical resistivity that is not uniform about their exposed surface. This non-uniform resistivity results in erroneous measurements since the voltage readings tend to be averages. This is especially true when the electrodes are subjected to high voltage gradients. Attempts to solve this problem have lead to the development of relatively costly structures either with a separate reference electrode or the incorporation of the reference electrode into existing electrodes. These devices utilize an annular element of porous material to close a cavity between the body portions of the reference and measuring electrodes to create an isolated cavity for the reservoir of electrolyte and a reference junction of uniform resistance over all radial segments. The ability to incorporate these types of structures in the commercial electrolytic cell has been difficult because of space requirements and the costs.

The development of wire reference electrodes has provided an approach that permits the electrode potentials to be monitored and recorded in commercial chloralkali electrolytic cells. However, prior wire reference electrodes have encountered the aforementioned durability problem, especially on the cathode side of the cell where the concentrated caustic solution tends to dissolve the wire. This is especially true in wire reference electrodes wherein a platinized platinum wire is employed. The dissolution because of the apparent high porosity of the exposed surface will occur over too short a period of time, often only several days, and limit the practical utility of these types of reference electrodes in commercially operating cells.

It has also been found that the seal around the wire separating the lead-in wire from the exposed reference wire portion in the wire reference electrodes is critical. It has been discovered that if electrolyte, especially the caustic solution, leaks backwardly between the exposed reference wire portion and the shielding that encases the lead-in wire, a second potential may be generated. This is particularly true at the weld point of the reference wire portion to the lead-in wire which is used so that the reference wire electrode may be connected over a substantially long distance to monitoring apparatus, such as volt meters, externally of the cell. Electrolyte solution wetting the weld joint will allow an electrochemical reaction, such as corrosion, so that there will be one potential at the wire reference electrode and another as a result of the reaction at the lead-in wire, despite the use of a polyfluorinated hydrocarbon insulating tube.

Where such reference wire electrodes have been utilized in the filter press membrane type of chloralkali electrolytic cells there is the potential for the electrodes to accidentally puncture the membranes, thereby reducing the efficiency of the cell operation. However, because of the utility of these wire reference electrodes to measure the total cell voltage, the anode-to-reference electrode, reference electrode-to-membrane-to-reference electrode, and the reference electrode-to-cathode voltages, continued efforts have now resulted in the solution of the aforementioned problems in the design of the present invention. This newly designed structure permits the electrode potentials to be monitored over extended periods of time in commercial cells, as well as permitting fast transient studies of the operating cell conditions to be made where Luggin capillaries and external reference electrodes are not useful because of the high impedance level present that distorts the output voltage signal.

SUMMARY OF THE INVENTION

It is an object of the present invention to provide an improved wire reference electrode that will permit the extended monitoring of the anode, cathode, and membrane or separator voltage during operation in commercial chloralkali electrolytic cells.

It is another object of the present invention to provide a method for monitoring independently and determining the condition of the anode, cathode, and the membrane or separator in chloralkali electrolytic cells.

It is a feature of the present invention that the wire reference electrode utilized in conjunction with the anode is comprised of a titanium lead-in wire that is connected to a titanium dioxide-ruthenium dioxide coated titanium wire for measuring anode potential.

It is another feature of the present invention that the wire reference electrode utilized in conjunction with the cathode is comprised of a titanium lead-in wire that is connected to a palladium/silver alloy wire that is a predetermined percent palladium and a predetermined percent silver for measuring cathode potential.

It is another feature of the present invention that the wire reference electrodes are secured to the electrode surface in at least one location via an electrolyte-resistant thread.

It is a further feature of the present invention that an improved heat-shrink material composed of an electrolyte-resistant outer sleeve with a fluorinated ethylene polymer (FEP) inner lining is applied to the lead-in titanium wire and a portion of the reference wire portion to provide a durable, leak-resistant seal.

It is yet another feature of the present invention that the reference wire electrode is inserted into a foramen in the desired electrode foraminous surface.

It is an advantage of the wire reference electrodes of the present invention that the anode, cathode and membrane or separator potentials may be monitored independently to determine the condition of each cell component by analyzing the anode-to-wire reference electrode, wire reference electrode-to-membrane-to-wire reference electrode, and wire reference electrode-to-cathode voltages.

It is another advantage of the present invention that the wire reference electrode may be positioned on an electrode surface so that it does not intrude into the electrode membrane gap or may be employed in a cell where there is not a gap between the membrane or separator and electrode without puncturing the membrane or separator.

It is a further advantage of the present invention that the improved heat-shrink seal employed avoids corrosion at the weld of the titanium lead-in wire to the titanium dioxide-ruthenium dioxide coated wire or the palladium silver alloy wire.

It is another advantage of the present wire reference electrodes that they may be utilized for fast transient studies of cell operating conditions where Luggin capillaries and separate external electrodes cannot be employed because of distortion to the voltage signal due to high impedance values.

It is yet another advantage of the present invention that the wire reference electrodes can be employed in commercial electrolytic cells to monitor performance of the individual cell components.

These and other objects, features, and advantages are obtained in the apparatus and the method of employing the apparatus of the present invention wherein a wire reference electrode having a lead-in wire of predetermined composition, a reference wire portion of predetermined composition connected to the lead-in wire at a first location, sealing means and heat shrinkable means collapsible about the sealing means to prevent the leakage of electrolyte solution into the first location is utilized in a plurality of locations within an electrolytic cell to monitor the operation of the cell components during extended operation.

BRIEF DESCRIPTION OF THE DRAWINGS

The advantages of this invention will become apparent upon consideration of the following detailed disclosure of the invention, especially when it is taken in conjunction with the following drawings wherein.

DETAILED DESCRIPTION OF THE PREFERRED EMBODIMENT

The improved wire reference electrode will be discussed hereinafter in conjunction with its usage in a chloralkali electrolytic cell, especially in conjunction with the foraminous electrode surfaces of such a cell. It is to be understood that the discussion of a foraminous electrode surface is intended to encompass both anode and cathode surfaces. It is also to be understood that the utilization of the improved wire reference electrode of the instant invention, while being discussed and exemplified in the context of a filter press membrane type of chloralkali electrolytic cell, could equally well be applied to a diaphragm type of chloralkali electrolytic cell, or any other type of electrolytic cell where it would be of value to monitor electrode potentials, providing that the specific metal composition selected for the wire is compatible with the electrolyte solutions.

Figure 1:
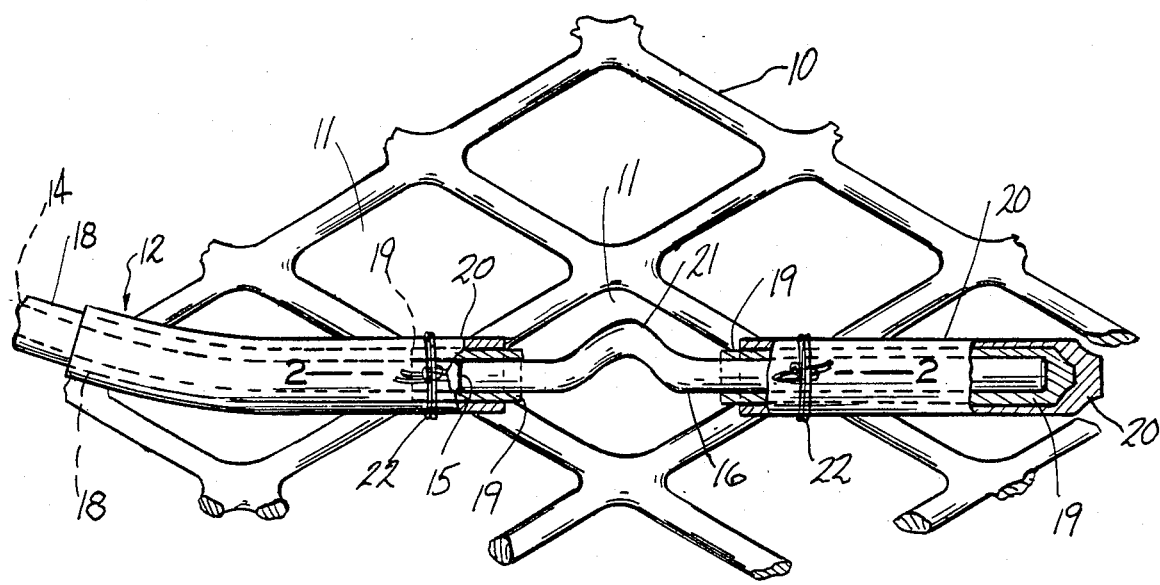
FIG. 1 is an enlarged perspective view of a portion of a foraminous electrode surface showing the wire reference electrode fastened thereto.

Looking at FIG. 1, there is shown a portion of a foraminous electrode surface 10 with individual foramen 11. The electrode surface 10 preferably is made from expanded mesh which is flattened. However, it is possible to use an expanded mesh which is unflattened, or a perforated plate, screen or other suitable materials. The composition of the material comprising the electrode surfaces is dependent upon whether an anode or a cathode is being discussed. The compositions are well known in the art. For example, typical anode electrode surfaces are made of titanium or tantalum with suitable coatings, while cathode electrode surfaces are made from nickel, iron, steel, or tantalum with suitable catalytic coatings. The preferred composition traditionally has been titanium for the anode electrode surfaces and nickel for the cathode electrode surfaces.

A wire reference electrode indicated generally by the numeral 12 in FIG. 1, is shown in part. The wire reference electrode is shown having a lead-in wire 14, which is shown in phantom lines. The lead-in wire 14 is typically made from titanium that is from about 20 to about 24 gauge. The lead-in wire is connected, such as by welding, at a location 15 to the reference wire portion 16 of the wire reference electrode 12.

The reference wire portion 16 in the cathode chamber is constructed of from about 20-24 gauge palladium/silver alloy wire. The alloy wire is comprised of approximately 75% palladium and approximately 25% silver and its preferred thickness is 24 gauge. The exact range of the percentages of palladium and silver which may be used in the reference wire portion 16 is variable. The operable composition of the reference wire portion 16 for a reference electrode purpose requires a minimum amount of silver to be present for the reason that will be explained hereinafter. Therefore, it is felt that a range of percentages of silver greater than 25%, as well as some finite percentage less than 25%, also will be suitable for the intended purpose. The palladium/silver alloy has the advantage of being durable when immersed in or subjected to a caustic solution, as well as providing a steady potential during cell operation.

The palladium silver alloy is known to absorb substantial amounts of hydrogen and causes a potential shift from the reversible hydrogen potential of approximately 50 millivolts in the environment of an electrolytic cell. However, this is a one time only shift and the potential, as previously mentioned, remains steady subsequent to the initial potential shift, thereby providing a reliable potential read-out for monitoring the cell operation. The presence of silver in the alloy stabilizes the palladium and serves to lock it into a single phase. This preserves the predetermined crystalline phase of palladium after an initial start-up procedure for charging the reference wire portion, which will be described hereinafter, is accomplished to build up hydrogen in the metal alloy. This charging of the palladium/silver alloy reference wire portion builds up the hydrogen which is absorbed in the surface to form a palladium hydride at a stable level. This charging process is particularly critical since in its absence it can take up to two weeks to build up the steady state concentration of hydrogen necessary to form the stable palladium hydride potential.

The anode reference wire portion is from about 20 to about 24 gauge titanium wire that has been appropriately coated. The preferred gauge is 22 gauge wire. The conductive reference wire portion 16 is comprised of a valve metal selected from the group consisting of tantalum, titanium, zirconium, bismuth, tungsten, niobium, and alloys thereof, such as for example, the aforementioned titanium wire, that is coated with a ruthenium chloride coating. The ruthenium chloride is used to produce a ruthenium dioxide-titanium dioxide mixed-crystal material in accordance with the teachings of U.S. Pat. No. 3,632,498, issued on Jan. 4, 1972, to H. B. Beer. The desired coating utilizes a mixed-crystal material consisting essentially of at least one oxide of a film-forming metal, such as titanium, and at least one oxide of a platinum group metal, such as ruthenium. The ruthenium chloride coating solution suitable to produce the desired ruthenium dioxide-titaniumdioxide coating for the titanium wire is for example as follows:

12.4 ml butanol
0.8 ml 36% HCl
6.0 ml Tetra-n-butyl-orthotitanate $(C_4H_8)_4Ti$
2.0 g.$RuCl_3$.

An exemplary preparation of the titanium wire is as follows. The appropriately sized gauge titanium wire is cleaned with acetone and then washed with soap and water. The titanium wire is then etched with concentrated (approximately 36%) hydrochloric acid (HCl) for 10 minutes and then rinsed with deionized water for about 10 to 20 minutes. The ruthenium chloride solution is applied to the titanium wire with a brush and fired in an oven from about 300° C. to about 500° C. for from about 1 to about 6 minutes, preferably at 400° C. for 5 minutes. This application and firing procedure is repeated four additional times. The titanium wire is then heated in air at from about 300° C. to about 500° C. for 4 to 8 hours, preferably at 400° C. for 6 hours. This produces the mixed crystal coating necessary for a reference electrode to be used in an anode.

The reference wire portion in the cathode chamber, preferably constructed of 24-gauge palladium silver alloy, is welded to the lead-in wire 14 of the previously mentioned titanium or nickel. The exposed cathode reference wire portion 16 of the wire reference electrode 12 is treated, for example, by immersing in a 70% nitric acid solution for several minutes, generally 1-10 minutes, to clean the surface prior to installation in a cell.

Where a long electrical lead-in wire 14 is required, a nickel or titanium wire, as appropriate, is spot-welded at the weld location 15 to the reference wire portion 16. The wire reference electrode 12 is then ready for sealing. The same procedure is utilized whether the wire reference electrode 12 is to be employed in an anode chamber or a cathode chamber. The lead-in wire 14 is inserted within an electrical insulator or tubing shield 18, preferably of polytetrafluoroethylene, such as that sold under the trademark Teflon ®, that extends to a point just short of the weld location 15 where it junctions with an inner layer of electrical insulator and sealant, preferably fluorinated ethylene polymer 19, hereinafter FEP. Atop and about the tubing shield 18 and the FEP 19 is an electrically insulating heat shrink tubing 20, preferably formed from polytetrafluoroethylene such as that sold under the trademark Teflon ®. As seen in FIG. 1, the FEP 19 extends for a short distance outwardly from beneath heat shrink 20. Adjacent the terminous of the FEP 19 is the exposed reference wire portion 16 which is shown as having a dimple or indentation 21 where it extends into a foramen 11 of the foraminous electrode surface 10.

On the opposing side of foramen 11, the exposed reference wire portion 16 is similarly sealed. An inner layer of FEP 19 surrounded with an electrically insulating heat shrink material 20, such as the aforementioned polytetrafluoroethylene.

Once the wire reference electrode 12 is wrapped with the FEP 19, the inner tubing shield 18 and the heat shrink 20, it is placed in an oven for approximately 3 minutes at approximately 270° C. to melt the FEP and to cause the heat shrink tubing to collapse. After removing the wire reference electrode 12 from the oven and allowing it to cool, the wire reference electrode 12 is ready to be mounted to the appropriate electrode surface. The wire reference electrode 12 is secured in place by suitable binding means, such as Teflon ® strings 22 shown in FIG. 1 on opposing sides of the foramen 11 into which the dimple or indentation 21 extends. Alternate heating means, such as a GL-O-RING available from the Rush Wire Stripper Division of the Eraser Company, Inc. of Syracuse, N.Y. or a LUX-THERM Little Shrink, manufactured by the Hi-Shear Corp. of Torrance, Calif. may be used to melt the FEP 19 and the heat shrink 20.

The sealing step is especially critical to the accuracy achieved with the reference electrode. Both the tubing shield 18 that covers the lead-in wire 14 and the FEP 19 serve as electrical insulators to prevent distortion or erroneous signals from being transmitted back to recording apparatus external of the cell when the wire reference electrode 12 is employed. The heat shrink 20 also serves as an additional electrical insulator. The FEP 19, however, primarily serves as a sealant to prevent caustic or other electrolyte from entering adjacent the exposed reference wire portion 16 and travelling upwardly to the weld at the weld location 15. If the caustic or other electrolyte leaks back up the wire to this location, inaccurate and distorted potential readings will result. For example, caustic corrosion can occur at the location of the titanium and the silver palladium wire interface that will cause the titanium weld to give a potential, but as a result of the titanium-caustic corrosion. There will also be a second potential at the exposed reference wire portion 16, the normal and desired location for measuring the potential. The wire reference electrode 12 will then measure the average of the reversible half reaction $2e^- + H_2O \rightleftharpoons 2OH^- + H_2$ at the reference electrode and a nonreversible titanium corrosion reaction such as $Ti \rightarrow Ti^{+++} \pm 3e^-$ at the weld where the titanium wire is welded to the titanium dioxide-ruthenium dioxide wire.

On the anode side if the electrolyte leaks back up into contact with the titanium and the titanium dioxide-ruthenium dioxide interface at the weld location 15, this will cause a potential different from the normal and desired sensed potential at the exposed wire reference portion 16. The wire reference electrode will then measure the average of the reversible half reaction $2e^- + Cl_2 \rightleftharpoons 2Cl^-$ and the reference electrode and the reaction $2e^- + Cl_2 \rightarrow 2Cl^-$ at the weld location 15 where the titanium wire is welded to the titanium dioxide-ruthenium dioxide wire.

This caustic corrosion on the cathode side is especially a problem in prior wire reference electrodes that have attempted to use only a polyfluorinated hydrocarbon insulating tube. Experience has shown that this single polyfluorinated hydrocarbon insulating tube tends to separate or develop small cracks along the length of the wire to which it is applied, thereby creating entrance ways for caustic to back flow along the reference wire to the weld location at the titanium and the palladium/silver interface. In the instant invention, the multiple layers of the electrical insulator and sealant FEP 19 and heat shrink 20 prevent the wire reference electrode 12 from being exposed along its length to caustic or other corrosive electrolyte that can corrode the interface or weld.

The materials employed to electrically insulate and seal the weld location 15 of the wire reference electrode 12 are commercially available. The FEP 19 may be purchased separately from the Resins Division of E. I. DuPont de Nemours & Co. of Wilmington, Del. The tubing shield 18 may be purchased from Bel-Art Products of Pequannock, N.J. The heat shrink 20 is available from Zeus Industrial Products, Inc. of Raritan, N.J. Heat shrink with an already assembled FEP liner is also commercially available from Zeus Industrial Products so that individual layers of FEP, heat shrink and tubing shield need not be applied. It is preferred to use the ready made heat shrink 20 with the liner of FEP 19 already inserted. Severe problems were encountered with the heat shrink tubing moving during the heating and shrinking process, especially when the FEP was separately wrapped about the wire in a very labor intensive operation. This movement exposed some wire to the caustic or other corrosive electrolyte and created the opportunity for corrosion to occur. Kynar ® fluorinated vinyl polymer, available from Penwalt Corporation is also suitable for use as an insulator when brushed on the reference wire electrode 12 that is to be used in the anode. For the reference wire electrode 12 that is to be in a cathode, chlorinated polyvinyl chloride (CPVC)

or polypropylene may be also employed as heat shrink material as suitable.

The positioning of the wire reference electrodes 12 adjacent to the appropriate electrode surface 10 affects the accuracy of the potential readings that are recorded. Along the edge of the electrode surfaces adjacent the electrode frame the voltage and current density may differ from the more uniform voltage and current density over the rest of the electrode surface. Also the nonuniform condition of the electrode surface may cause redistribution of current and potential so that the measured potential is nonrepresentative. This nonuniform condition of the electrode surface can be the result of leaching out of alloys, such as aluminum or molybdenum, from the cathode surface and pitting in the anode surface. The placement of the wire reference electrode 12 at the edge of the electrode surface is normally not desirable because of the current distribution edge affect which tends to cause an increase in the voltage readings at this point.

Therefore, the preferred location for positioning the wire reference electrode 12 with respect to an electrode surface 10 to obtain a steady potential reading has been determined to be approximately in the middle of the appropriate electrode surface along its horizontal dimension and about $\frac{1}{3}$ to $\frac{1}{2}$ of the way up its vertical dimension. This vertical positioning of the reference electrode tends to minimize the exposure of the electrode to product gas bubbles which affect the flow of the current in the area adjacent the reference electrode. The current flow is affected since it must flow around bubbles and cannot go through the bubbles since each bubble creates a break in the continuity of the electrolyte fluid. However, it should be emphasized that by positioning the electrode preferably $\frac{1}{3}$ of the way up the vertical dimension of the appropriate electrode surface, continuous and generally accurate readings of the potential may be obtained at the desired location.

Figure 2:
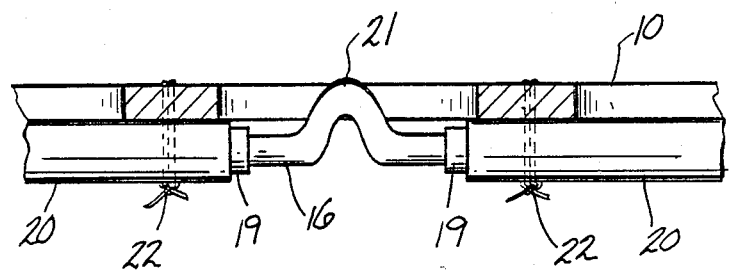
FIG. 2 is an enlarged sectional view taken along the lines 2—2 of FIG. 1 illustrating the relative positioning of the exposed wire portion of the wire reference electrode and the electrode surface.

For wire reference electrodes 12 of the dimple style or design shown in FIG. 1, the ideal position is to place the dimple 21 into the potential gradient between the anode surface and the membrane or separator, or the cathode surface and the membrane or separator, as appropriate. By inserting the dimple 21 of the reference electrode into the diamond shaped space or foramen 11 in the mesh of electrode surface 10, as seen in FIGS. 1 and 2, and, therefore, into the potential gradient, the most accurate potential readings are obtained. Alternately, the reference wire electrode shown in FIG. 3, utilizing a straight exposed reference wire portion 16 wrapped within an FEP layer 19 adjacent a tubing shield 18, both of which are covered with the heat shrink 20 over the area of the weld location (not shown), may be employed. In this embodiment, the wire reference electrode 12 is placed flat onto the mesh surface between the electrode surface 10 and the membrane so it overlies the desired foramen with the exposed reference wire portion 16 extending along the longer axis of the foramen, which is seen in FIG. 1 to be generally horizontally.

Figure 3:
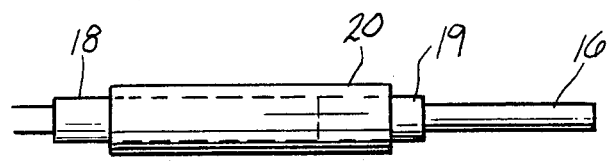
FIG. 3 is an alternative embodiment of the wire reference electrode showing the exposed reference wire portion that can be extended into a foramen of the foraminous electrode surface.

Regardless of whether the dimple style of wire reference electrode 12 or the straight style shown in FIG. 3 is employed, it has been found to be advantageous to ensure that the exposed reference wire portion 16 extends along the longer or major axis of the diamond shaped foramen 11. As just mentioned, this is seen in the instant case in FIG. 1 to be generally horizontal. The wire reference electrodes 12 may be mounted in an electrolytic cell in several ways to obtain this orientation. The wire reference electrode 12 may be tied to the front side of the electrode surface 10 so that it is interposed between the electrode surface 10 and the adjacent membrane or separator (not shown). It has been preferred to secure the wire reference electrode 12 employing the dimple or indented style to the back side of the electrode surface 10 so that the indentation or dimple 21 extends through one of the diamond shaped foramen 11, placing the exposed reference wire portion 16 in essentially the same plane as the electrode surface 10. This manner of mounting is best exemplified in FIG. 2.

The wire reference electrode 12 is secured in place, regardless of the specific mounting locations to the electrode surface by the use of the polytetrafluoroethylene thread or string 22. Where the dimple or indented style of wire reference electrode 12 is employed, two polytetrafluoroethylene threads or strings 22 are employed on either side of the exposed wire portion 16, as seen in FIGS. 1 and 2. This method is desirable to anchor the wire reference electrode 12 as securely as possible to the electrode surface 10 to prevent movement or drift of the exposed reference wire portion 16 during cell operation. Such movement may be caused by tension on the lead-in wire or by the flow of the electrolyte and gas bubbles upwardly through the electrodes during operation and is to be avoided because any repositioning of the wire reference electrode will affect the accuracy of any potential readings since the wire reference electrode will be moving with respect to the potential gradient. Should the exposed reference wire portion 16 actually touch the electrode surface 10, the measured potential will, in effect, be shorted out.

Alternately, the wire reference electrode 12 of the instant invention can also be separated from the appropriate electrode surface 10 by installing it next to the membrane or separator (not shown) by insertion into a small groove in the gasket (not shown) that is employed between adjacent electrode frames so that the wire reference electrode 12 is on or closely adjacent to the membrane or separator.

In order to exemplify the results achieved, the following examples are provided without any intent to limit the scope of the instant invention to the discussion therein. The first three examples are intended to illustrate how comparison data can be obtained from operating cells using a wire reference electrode and the reliability or accuracy of such data.

EXAMPLE I

An approximately 0.28 square meter pilot cell was operated at approximately 3.0 kA/m$^2$ current density with approximately 32.0% sodium hydroxide concentration at 90° C. The following voltage readings were obtained:

Cathode vs. Pd/Ag—0.589 V

Anode vs. Ti—0.309 V

Pd/Ag vs. Ti—3.04 V

Total—3.978 V

Cell (Measured)—3.94 V

EXAMPLE 2

An approximately 0.28 square meter pilot cell was operated at approximately 3.0 kA/m² current density with approximately 33.7% sodium hydroxide concentration at approximately 90° C. The following voltage readings were obtained:

Cathode vs. Pd/Ag—0.571 V

Anode vs. Ti—0.305 V

Pd/Ag vs. Ti—3.10 V

Total—3.929 V

Cell (Measured)—4.05 V

EXAMPLE 3

An approximately 0.28 square meter pilot cell was operated at approximately 2.0 kA/m² current density with approximately 31.1% sodium hydroxide concentration at approximately 90° C. temperature. The following voltage readings were obtained:

Cathode vs. Pd/Ag—0.325 V

Anode vs. Ti—0.160 V

Pd/Ag vs. Ti—3.28 V

Total—3.773 V

Cell (Measured)—3.77 V

For each of the above examples, the measured cell voltage was obtained by using a volt meter that was connected to sampling leads or taps on the lead-in bus to both the anode and the cathode. The palladium/silver versus titanium reading represents the potential reading in the area of the separator or membrane. In this case, an ion-selective membrane, manufactured by E. I. DuPont de Nemours & Company and sold under the trademark Nafion ®, was inserted between each anode and cathode. The surfaces of the anodes and cathodes typically were catalytically coated titanium and nickel, respectively. Each cell used only one anode and cathode.

The cathode surfaces and the anode surfaces were referenced against the appropriate wire reference electrode, palladium/silver for the cathode and ruthenium dioxide-titanium dioxide coated titanium for the anode. The wire reference electrodes 12 were of the dimple style and were mounted in the center of the diamond shaped foramen 11 in the mesh electrode surfaces 10 from the rear, as illustrated in FIGS. 1 and 2. The cathode versus the palladium/silver readings give the potential at the cathode surface while the anode versus the titanium readings give the potential at the anode surface. The palladium/silver versus the titanium voltage readings give the potential at the membrane and were determined by measuring the potential between the two wire reference electrodes. In each case the sum of the voltage readings at the cathode, anode, and the membrane give a total that is essentially equivalent to the measured cell voltage using the volt meters, differing only from a high of 0.121 volts to a low of 0.003 volts. In the case of Example 3, a lower total cell voltage was obtained when compared to the readings obtained in Examples 1 and 2, but this was expected because of the lower current density employed. The lower relative cathode and anode recorded voltages combined with a higher membrane voltage in Example 3 were probably due to a shift in the reference electrode potential of one of the wire reference electrodes 12.

The significant fact, however, from all of the data is the accuracy obtained by use of the reference electrode, comparing the total cell voltage obtained by summing the individual measured wire reference electrode readings to that measured with a volt meter.

EXAMPLE 4

An approximately 4 square meter filter press membrane chloralkali cell was operated at approximately 3.0 kA/m² current density with a designed sodium hydroxide concentration of approximately 33.0% at 90° C. The filter press membrane chloralkali cell employed four ion-selective membranes, manufactured by E. I. DuPont de Nemours & Company and sold under the trademark Nafion ®, between adjacent anodes and cathodes. Each end cathode was a half cathode so that each anode was sandwiched between adjacent cathodes. The surfaces of the cathodes included nickel and the anodes were made from titanium. Wire reference electrodes 12 were inserted between each cathode surface and the adjacent membrane and each anode surface and the adjacent membrane. This permitted the cathode surfaces and the anode surfaces to be referenced against the appropriate wire reference electrodes; palladium/silver for the cathode and ruthenium dioxide-titanium dioxide coated titanium for the anode. The wire reference electrodes 12 were the dimple style and were mounted in the center of the diamond shaped foramen 11 in the mesh electrode surfaces 10 from the rear, as illustrated in FIGS. 1 and 2. The cathode versus the palladium/silver readings gave the potential at the cathode surface while the anode versus the titanium readings gave the potential at the anode surface. The palladium/silver versus the titanium voltage readings gave the potential at the membrane and included the potential at the membrane and the electrolyte. These readings for three of the four subcells are reflected in FIG. 4. A subcell is defined as a cathode surface-membrane-anode surface grouping. Only three of the four subcells are shown because the data for the fourth subcell was not reliable because of technical problems with the reference electrodes.

Figure 4:
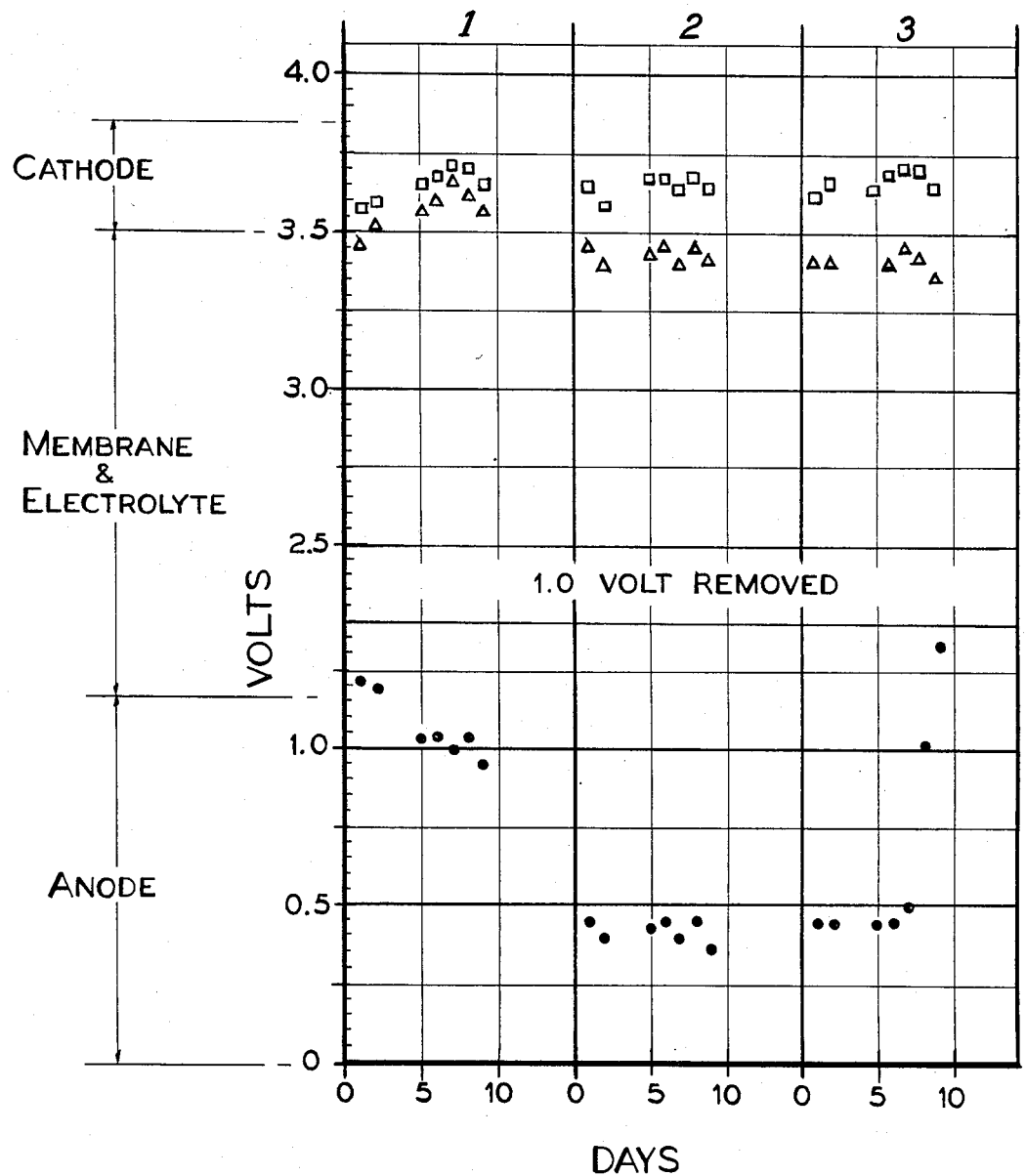
FIG. 4 is a graphical illustration showing the voltage values obtained for three electrolytic subcells during operation of a filter press electrolytic cell to illustrate the monitoring value of such wire reference electrodes.

The voltage readings shown on the graph in FIG. 4 were obtained utilizing the principles shown in the following equations:

$$E\ Anode = (E_{oCl_2} - E_{RE}) + IR + OV$$

$$E\ Cathode = (E_{oH_2} - E_{RE}) + IR + OV$$

$$E\ Membrane = V_{IR} + V[A-C] + (E_{RE}\ cathode - E_{RE}\ anode)$$

The voltage measured at the anode is equal to the potential of the reversible chlorine reaction at the anode minus the potential of the reference electrode plus the IR drop and the overvoltage necessary to drive the anodic reaction. The potential at the cathode is equal to the potential of the reversible hydrogen reaction at the cathode minus the potential of the reference electrode plus the IR drop and the over-voltage necessary to drive the cathodic reaction. The potential of the membrane and the electrolyte is equal to the potential drop across the membrane plus the concentration difference potential of the anolyte and the catholyte fluids plus the difference of the cathode reference potential and the anode reference potential.

The use of the reference wire electrodes of the instant invention in the cell enabled the operation of the cell to be monitored as a whole, as well as through the monitoring of the voltage of the individual components of the cell, to enable detection of any faulty components. The monitored three subcells are divided along the horizontal axis of the graph in FIG. 4 to show the results over 10 days of operation. The anode voltage readings are shown on the graph of FIG. 4 by the darkened circles, the cathode voltage readings by the hollow rectangles or squares, while the combined membrane and electrolyte voltage is shown by the hollow triangles.

The data from subcell 1 shows high anode voltage in comparison to the subcells 2 and 3. Concurrently, the membrane and electrolyte voltage and cathode voltage appear to be low in comparison to the other two subcells shown. This is the pattern of voltage distribution that is to be expected if the anode is not properly performing for some reason and has an unusually high resistance. When this occurs, a filter press membrane cell will distribute the total current among its subcells so that each subcell has the same voltage. If subcell 1 has a high resistance, some of its current will be portioned off to the remaining subcells. Accordingly, instead of experiencing the designed operating current density of 3 kA/m$^2$, the cell probably is experiencing a current density of about 3.5 kA/m$^2$ in the two subcells which had normal resistance. This current density is not obtained directly from the wire reference electrodes 12 of the instant invention, but may be found by comparing data tables from the same sized cells where the recorded cathode voltage is the same.

The anode measurement for subcell 3 showed a drift that started after several days, but which did not affect the total cell voltage. The exact cause for this drift is unknown, but it is theorized that the anode wire reference electrode 12 was no longer at the reversible chlorine potential.

When the operation of this particular cell was terminated and the cell was broken apart, it was found that part of the electrical connection to the first anode had failed and was the cause of the high anode voltage. Thus, by utilizing the wire reference electrodes 12 of the present invention, it was possible to diagnose the exact faulty component during operation. Previously where cell voltage, cell current, cell current efficiency, and power consumption were used as indicators of cell performance, only the condition of the cell as a whole could be determined. In instances such as the one specifically encountered in this example, where one of the portions of the cell begins to fail due to poor operation or faulty component, the operator previously could only guess at the nature and location of the problem in attempting to correct it. With the aid of the monitoring capability of the wire reference electrodes 12, it was possible to determine that the high cell voltage was caused by the specific anode problem of subcell 1. This was obvious because the expected anode voltage should have been approximately 0.4 or 0.45 volts, instead of the approximately 1.0 to 1.05 voltage readings obtained.

Thus, it can be seen how monitoring the voltage of the individual components of the cell can pinpoint problems that occur within the cell during operation and enable quick replacement or correction of the defective components.

It should also be noted that the wire reference electrodes utilized in both the anode compartment and the cathode compartment can be reused with some maintenance between usage. For example, the palladium/silver wire reference electrode used in a cathode compartment should be immersed in a 70% concentrated nitric acid solution for approximately 1 to 5 minutes before being reused. The palladium/silver wire reference electrode also must be charged prior to use in a cell, whether the electrode has been restored or is being used initially. This procedure requires that after the electrolyte has been added to the electrolytic cell, the palladium/silver wire reference electrode 12 is connected to the negative lead of a power source and the positive lead of the power source to the cell anode. A charge of approximately 100 mA is maintained for approximately 10 minutes to charge the palladium/silver wire reference electrode while hydrogen evolves from the wire surface.

The ruthenium-chloride coated electrode that is utilized in the anode chamber requires no charging. However, this wire reference electrode can be restored for normal use by cleaning with soap and water with a soft bristle brush. If the ruthenium dioxide-titanium dioxide coating is scraped or worn off, however, the electrode must be recoated according to the procedure described in detail earlier, or discarded. If the ruthenium dioxide-titanium dioxide coating is faulty or it is required to strip the old coating from the wire, this can be accomplished by soaking the wire reference electrode in an Aqua Regia solution (75% HCl + 25% HNO$_3$) for approximately ten minutes.

While the preferred structure in which the principles of the present invention have been incorporated is shown and described above, it is to be understood that the invention is not to be limited to the particular details thus presented, but in fact widely different means may be employed in the practice of the broader aspects of this invention. The scope of the appended claims is intended to encompass all obvious changes in the details, materials, and arrangement of parts, which will occur to one of skill in the art upon a reading of the disclosure.

Having thus described the invention, what is claimed is:

1. An electrolytic cell having a wire reference electrode immersed in an electrolyte solution for use in the electrolytic cell, the cell having at least a first foraminous cathode surface with foramens of a predetermined height and a second foraminous anode surface with foramens of a predetermined height separated by an ion-selective permeable separator, the combination comprising:
   a. a lead-in wire of predetermined size and composition, the lead-in wire being connectable to a voltmeter;
   b. a reference wire portion connected to the lead-in wire at a first location, the reference wire portion being of a predetermined size and composition and extending along and at least partially into a foramen;
   c. sealing means for sealing the lead-in wire, the first location and at least a portion of the reference wire portion from the electrolyte solution; and
   d. heat shrink means collapsed about the sealing means to cover at least a portion of the sealing means when subjected to a predetermined level and manner of heating.

2. The apparatus according to claim 1 wherein the reference wire porition is generally straight.

3. The apparatus according to claim 1 wherein the reference wire portion is indented so that the indentation is projected into a foramen.

4. The apparatus according to claims 2 or 3 wherein the foramen is approximately one-third of the distance up the predetermined height of the cathode surface.

5. The apparatus according to claims 2 or 3 wherein the foramen is approximately one-third of the distance up the predetermined height of the anode surface.

6. The apparatus according to claim 5 wherein the reference wire portion is titanium coated with a titanium dioxide and ruthenium dioxide coating.

7. The apparatus according to claim 3 wherein the reference wire portion is approximately 75% palladium and approximately 25% silver alloy.

8. The apparatus according to claim 3 wherein the reference wire portion is a palladium silver alloy.

9. The apparatus according to claim 3 wherein a portion of the reference wire portion located at a greater distance from the first location than the indentation is surrounded by a second sealing means so that the identation lies between the first sealing means and the second sealing means.

10. The apparatus according to claim 9 wherein the second sealing means is surrounded by a second collapsed layer of heat shrink means.

11. The apparatus according to claim 10 wherein the second collapsed layer of heat shrink means is electrically insulating.

12. The apparatus according to claim 11 wherein the second collapsed layer of heat shrink means is polytetrafluoroethylene.

13. The apparatus according to claim 10 wherein the reference electrode is mounted to the foraminous cathode surface by binding means at least at the heat shrinkable means.

14. The apparatus according to claim 13 or 11 wherein the reference wire electrode is mounted by a second binding means at the second collapsed layer of heat shrink means.

15. The apparatus according to claim 14 wherein the second binding means is thread made of polytetrafluoroethylene.

16. The apparatus according to claims 13 or 11 wherein the binding means is thread made of polytetrafluoroethylene.

17. The apparatus according to claim 10 wherein the reference electrode is mounted to the foraminous anode surface by binding means at least at the heat shrink means.

18. The apparatus according to claim 9 wherein the second sealing means is a fluorinated ethylene polymer.

19. The apparatus according to claim 2 wherein the reference electrode is mounted to the foraminous cathode surface by binding means.

20. The apparatus according to claim 2 wherein the reference electrode is mounted to the foraminous anode surface by binding means.

21. The apparatus according to claim 19 or 20 wherein the binding means is thread made of polytetrafluoroethylene.

22. The apparatus according to claim 1 wherein the lead-in wire is made of titanium.

23. The apparatus according to claim 1 wherein the sealing means is a fluorinated ethylene polymer.

24. The apparatus according to claim 1 wherein the heat shrink means is electrically insulating.

25. The apparatus according to claim 24 wherein the heat shrink means is polytetrafluoroethylene.

26. The apparatus according to claim 1 wherein the reference electrode further comprises an electrically insulating tubing shield of predetermined length surrounding at least the lead-in wire and adjacent the sealing means.

27. The apparatus according to claim 26 wherein the tubing shield is polytetrafluoroethylene.

28. An electrolytic cell having a wire reference electrode at a location adjacent foremens in an electrode where measurements are desired, comprising in combination:
 a. a lead-in wire of predetermined size and composition, the lead-in wire being connectable to a voltmeter;
 b. a reference wire portion connected to the lead-in wire at a first location, the reference wire portion being of a predetermined size and composition, the reference wire portion further being positioned adjacent and extending along and at least partially into a foramen;
 c. sealing means completely surrounding the lead-in wire for sealing the lead-in wire, the first location and at least a portion of the reference wire portion from liquid contact; and
 d. heat shrinkable means collapsed about at least a portion of the sealing means when subjected to a predetermined level and manner of heating.

29. A gas generating electrolytic cell having electrodes and a wire reference electrode used at least for measuring potential at predetermined locations in the electrolytic cell, the wire reference electrode having a lead-in wire connectable to a voltmeter and a reference wire portion connected to the lead-in wire at a first location, the improvement comprising in combination:
 a. sealing means surrounding and sealing from liquid contact a portion of the reference wire portion, the first location and at least a portion of the lead-in wire, the sealing means further having heat shrinkable means collapsed about at least a portion of the sealing means when subjected to a predetermined level and a manner of heat; and
 b. the reference wire portion being adjacent a foramen in an electrode and extending along and at least partially into the foramen.

30. The apparatus according to claims 28 or 29 wherein the sealing means is electrically insulating.

31. The apparatus according to claim 30 wherein the sealing means is a fluorinated ethylene polymer.

32. The apparatus according to claim 30 wherein the heat shrinkable means is polytetrafluoroethylene.

33. The apparatus according to claims 28 or 29 wherein the heat shrinkable means is electrically insulating.

34. The apparatus according to claims 28 or 29 wherein the reference wire portion is a palladium silver alloy.

35. The apparatus according to claim 34 wherein the alloy is approximately 75% palladium and approximately 25% silver.

36. The apparatus according to claim 34 wherein the lead-in wire is nickel.

37. The apparatus according to claims 28 or 29 wherein the reference wire portion is titanium with a titanium dioxide-ruthenium dioxide coating.

38. The apparatus according to claims 28 or 29 wherein the lead-in wire is titanium.

39. The apparatus according to claims 28 or 29 wherein the reference wire portion is indented.

40. The apparatus according to claim 39 wherein the reference wire portion further extends beyond the indentation a predetermined distance.

41. The apparatus according to claim 40 wherein the reference wire portion beyond the indentation further is surrounded by second sealing means.

42. The apparatus according to claim 41 wherein the second sealing means is a fluorinated ethylene polymer.

43. The apparatus according to claim 42 wherein the second sealing means further is surrounded by second heat shrinkable means that is collapsed when subjected to a predetermined level and manner of heating.

44. The apparatus according to claim 43 wherein the second heat shrinkable means is polytetrafluoroethylene.

* * * * *

UNITED STATES PATENT AND TRADEMARK OFFICE
CERTIFICATE OF CORRECTION

PATENT NO.  : 4,500,402
DATED       : February 19, 1985
INVENTOR(S) : Miles et al It is certified that error appears in the above-identified patent and that said Letters Patent is hereby corrected as shown below:

In column 7, at line 49 please delete "Teflon®" and insert --polytetrafluoroethylene--.

In column 15, at line 4 please delete "porition" and insert --portion--.

In column 15, at line 4 please insert after "straight" and before the punctuation mark " . " --and positionable adjacent a foramen--.

Signed and Sealed this

Eleventh Day of June 1985

[SEAL]

Attest:

DONALD J. QUIGG

Attesting Officer    Acting Commissioner of Patents and Trademarks